US005601817A

United States Patent [19]

Sztejnberg et al.

[11] Patent Number: 5,601,817

[45] Date of Patent: Feb. 11, 1997

[54] **CONTROLLING OOMYCETE-CAUSED DISEASES IN PLANTS USING *FUSARIUM PROLIFERATUM***

[75] Inventors: Abraham Sztejnberg, Rehovot, Israel; Roger C. Pearson, deceased, late of Geneva, N.Y., by Karen Pearson, executrix

[73] Assignee: Cornell Research Foundation, Inc., Ithaca, N.Y.

[21] Appl. No.: 381,150

[22] Filed: Jan. 30, 1995

Related U.S. Application Data

[63] Continuation of Ser. No. 242,978, May 16, 1994, abandoned.

[51] Int. Cl.[6] .......................... A01N 63/04; A01N 63/00; C12N 1/14

[52] U.S. Cl. .................. 424/93.5; 435/254.1; 435/254.7; 435/911; 435/929

[58] Field of Search ................................ 435/254.1, 911, 435/929, 254.7; 424/93.5

[56] References Cited

PUBLICATIONS

Falk, S. P. et al., Phytopathology, vol. 85(10), p. 1147, abs. #260. 1995.

ATCC Catalogue of Filamentous Fungi, 18th ed., 1991, ed. S. C. Jong et al. p. 188.

H.–D. Bourquin, "Communications from the Fed. Biological Inst. for Agriculture and Forestry", #223, Oct. 1984, Berlin–Dahlem p. 178 (translation).

E. I. Andreeva, "Mikologiya: Fitopatologiya," vol. 13, #2, 1979, pp. 89–94 (translation).

Boqdanova, V. N. et al, "Mikroorganizmy Virusy," 1979, pp. 43–50 (translation).

Alexopoulos, C. J., et al, Introductory Mycology, 3rd ed., John Wiley & Sons, New York, NY 145–188, 1979.

Marasas, W. F. O., et al, Mycologia 80(3), 407–410, 1988.

Nelson, P. E., et al, Mycologia 82(5), 562–565, 1990.

Jindal, K. K. et al. (Abstract) Indian J. Plant Pathol. 6:59–62 (1988) #1.

Magie, R. O., Proc. Fla. State Hortic. Soc. 93:172–175 (1980).

Mildenhall, J. P., et al, (abstract) Phytophylactica 17:54 (1985).

Rao, N. N. R., et al, Can. J. Bot. 54:220–223 (1976).

Viljoen, A., et al, Plant Dis. 79:1240–1244 (1995) #12.

*Primary Examiner*—Michael G. Wityshyn
*Assistant Examiner*—Kristin Larson

[57] ABSTRACT

Oomycete-caused plant disease, e.g., downy mildew, is controlled using *Fusarium proliferatum*, and biologically pure cultures of *Fusarium proliferatum* strains G6, M3, C51 and C173 respectively having accession numbers ATCC 74149, ATCC 74273, ATCC 74274 and ATCC 74275 are provided.

16 Claims, No Drawings

CONTROLLING OOMYCETE-CAUSED DISEASES IN PLANTS USING *FUSARIUM PROLIFERATUM*

This application is a continuation of application Ser. No. 08/242,978, filed May 16, 1994, now abandoned.

TECHNICAL FIELD

This invention is directed to the use of the fungus *Fusarium proliferatum* to control plant pathogenic fungi belong to the taxonomic class Oomycetes (sensu, Alexopoulos, C. J., et al, Introductory Mycology, 3rd Ed., 1979, John Wiley and Sons, N.Y., N.Y., pp 145–188).

BACKGROUND OF THE INVENTION

Several of the most destructive diseases of important crop plants are caused by members of the taxonomic class Oomycetes, such as downy mildew (*Plasmopara viticola*) which affects grapes, and late blight (*Phytophthora infestans*) which affects potatoes. Control of most of these diseases is generally achieved by the repeated application of chemical fungicides. This form of control is often problematic. Chemical pesticides may be phytotoxic or may injure the plant to which they are applied under certain environmental conditions. Certain fungicides are perceived as undesirable by consumers and/or processors. For example, mancozeb and captan, two of the most effective chemical fungicides used against oomycetous plant pathogens, although allowed by the Environmental Protection Agency, are restricted or prohibited by major grape processors in the eastern United States. Furthermore, the development of resistance to certain chemical fungicides by oomycetous plant pathogens has limited the degree of disease control that can be achieved by their use. Metalaxyl, a newly developed fungicide, is no longer effective against grape downy mildew or potato late blight in many areas due to development of resistant strains of the pathogens.

There is therefore a need for alternative methods of controlling oomycetous plant pathogens. The present invention satisfies this need.

SUMMARY OF THE INVENTION

In one embodiment of the invention, there is provided a method for controlling oomycete-caused plant disease which comprises applying to the plant surfaces to be protected an oomycete-inhibiting amount of a biocontrol agent, namely, *Fusarium proliferatum,* very preferably *Fusarium proliferatum* strain G6. In preferred modes of operation, the *Fusarium proliferatum* is applied as a suspension of spores sprayed on the plant surfaces to be protected, at 7–14 day intervals, and the plants are grapevines, e.g., of the Vitis interspecific hybrid cultivar Chancellor, and the species of Oomycetes inhibited is *Plasmopara viticola* (which causes grape downy mildew).

In other embodiments of the invention, there are provided biologically pure cultures respectively of the biocontrol agents *Fusarium proliferatum* strains G6, M3, C51 and C173.

The term "control" is used herein to mean prevent or alleviate.

The term "protect" is used herein to mean to prevent plant surfaces from being infected or colonized by disease causing oomycete fungus and/or to eradicate such disease causing fungus from the infected or colonized tissue.

The term "inhibit" is used herein to mean reduce the replication, germination or growth of the pathogenic oomycetous fungus.

The term "oomycete" is used herein to mean plant pathogenic fungus of the taxomonic class Oomycetes.

The term "oomycete inhibiting amount" connotes application of a suspension of $1\times10^5$ to $1\times10^7$ spores per ml or equivalent thereof for powder compositions to the entire plant surfaces to be protected.

DETAILED DESCRIPTION

The method of the invention herein is applicable to a wide variety of oomycete-caused plant diseases. These include grape downy mildew (caused by *Plasmopara viticola*) and potato late blight (caused by *Phytophthora infestans*) and oomycete infestation of Arctotis (caused by *Bremia lactucae*), *Chenopodium murale* (caused by *Peronospora farinosa*), cucurbits and cucumbers (caused by *Pseudoperonospora cubensis*), grasses and grains (caused by *Sclerospora graminicola*), lettuce (caused by *Bremia lactucae*), onion (caused by *Peronospora destructor*), alfalfa (caused by *Peronospora trifoliorum*), lima bean (caused by *Phytophthora phaseoli*), sunflower (caused by *Plasmopara halstedii*), carrot (caused by *Plasmopara nivea,* also called *Plasmopara crustosa*), hops (caused by *Pseudoperonospora humuli*), crucifers (caused by *Peronospora parasitica*), spinach (caused by *Peronospora effusa*), beet (caused by *Peronospora schachtii,* also called *Peronospora farinosa*), peas (caused by *Peronospora viciae*), rose (caused by *Peronospora sparsa*), poppy (caused by *Peronospora arborescens*), tobacco (caused by *Peronospora hyoscami*), and violet (caused by *Peronospora violae*).

All strains of *Fusarium proliferatum* are considered to be useful for the method of the invention herein. Preferred strains are *Fusarium proliferatum* strains G6, M3, C51 and C173; these were found on grape leaves in Geneva, N.Y. and selected and isolated by the inventors herein.

*Fusarium proliferatum* strains G6, M3, C51 and C173 have been deposited in accordance with the Budapest Treaty with the American Type Culture Collection, 12301 Parklawn Drive, Rockville, Md. 20852, U.S.A., and have been respectively assigned accession numbers ATCC 74149, ATCC 74273, ATCC 74274 and ATCC 74275. Strain G6 was deposited on Apr. 3, 1992. Strains M3, C51 and C173 were deposited on Mar. 11, 1993.

Application can be either of propagules or vegetative body (mycelium) of *Fusarium proliferatum.*

A biologically pure culture of spores of *Fusarium proliferatum* is readily provided by culturing in liquid medium, e.g., potato dextrose broth or malt dextrose broth, or in semisolid medium, e.g., potato dextrose agar, at room temperature. The product is preferably stored at 4° C. until use.

Mycelia of *Fusarium proliferatum* are readily produced in a fermentation process, e.g., by growth in Potato Broth Medium (described in Tuite, J., Plant Pathological Methods, Burgess Publishing Company, Minneapolis, 1969, at page 53) with agitation for 2–3 weeks at 25° C.

*Fusarium proliferatum* can be readily applied as a water suspension, e.g , at a concentration of $1\times10^5$ to $1\times10^7$, preferably $1\times10^6$, spores/ml. Emulsifying agent, e.g., TWEEN 20, (sorbitan monolaurate polyoxyalkylene) can be included to stabilize the suspension, to foster more uniform application. Alternatively, *Fusarium proliferatum* can be applied in a powder, e.g., with an agriculturally acceptable adhesive carrier, e.g., methyl cellulose or gum arabic.

The plant surfaces needing protection are those affected by an oomycetous pathogen. For grapevine, these include leaves, shoots, flowers and fruit. For potato, cucumber, onions and lettuce, these include all above ground parts. Preferably, *Fusarium proliferatum* is applied to plant surfaces to be protected by application thereof to the entire above-ground portion of the plant.

Application of a water suspension of *Fusarium proliferatum,* to a plant to be protected, is preferably carried out by spraying the entire above-ground portion of the plant. In the case of grapevines, this is very preferably carried out by spraying to runoff, e.g., application of approximately 0.5 liter of a suspension of $1\times10^6$ spores of *Fusarium proliferatum* to each grapevine at the beginning of the season and approximately 1 liter of a suspension of $1\times10^6$ spores of *Fusarium proliferatum* to each grapevine at the end of the season.

As indicated above, *Fusarium proliferatum* is applied to plant surfaces to be protected in an oomycete inhibiting amount. Preferably, this ranges from $1\times10^3$ to $1\times10^5$ spores per square centimeter of plant surface.

Application is preferably at 7 to 14 day intervals.

*Fusarium proliferatum* is somewhat compatible with many chemical fungicides, i.e., such chemical fungicides, in normally used levels, do not entirely inhibit the germination and growth of *Fusarium proliferatum.* BENLATE (benomeyl), BAYLETON and NOVA (myclobutanil) had the most detrimental effect on growth of *Fusarium proliferatum* strain G6 and copper sulfate, ALIETTE (phosethyl Al) and RIDOMIL (metalaxyl) had the least detrimental effect on growth of *Fusarium proliferatum* strain G6. Copper and sulfur fungicides had the least effect on spore germination. Captan had little effect on spore germination of *Fusarium proliferatum* strain G6 at 1 and 10 ppm and mancozeb allowed about 40% germination of *Fusarium proliferatum* strain G6 at 1 ppm.

Application of *Fusarium proliferatum* is considered safe. Fumonisins were not detected by HPLC/fluorescence (<0.5 μg/ml) in G6 treated grape berries or in juice prepared therefrom.

Scanning electron micrographs show hyphae of *Fusarium proliferatum* strain G6 coiling around and adhering to the oomycetous pathogen of grapevines, *Plasmopara viticola,* on application of G6 thereto. Transmission electron micrographs shows hyphae of *Fusarium proliferatum* strain G6 inside sporangiophores of *Plasmopara viticola.* Coiling and parasitism of *Fusarium proliferatum* strain G6 vis-a-vis *Phytophthora infestans,* similar to that vis-a-vis *Plasmopara viticola,* is shown via electron microscopy.

The invention is illustrated by the following Examples.

For Example I, *Fusarium proliferatum* strain G6 was produced as follows: *Fusarium proliferatum* strain G6 was grown on potato dextrose agar in petri dishes at room temperature. After 2–3 weeks, the mycelial mat containing microconidia was scraped from the surface of the agar and placed in distilled water. The suspension was homogenized on a vortex mixer and filtered through a double layer of cheesecloth. The spore suspension was adjusted to $1\times10^6$ spores/mi.

For Example II, *Fusarium proliferatum* strain G6 was produced as follows: The *Fusarium proliferatum* strain G6 was grown on potato dextrose agar in petri dishes at 24° C. in the dark. After 2–3 weeks, the mycelium with microconidia was scraped from the surface of the agar, shaken in a large flask of distilled water and filtered through 2 layers of cheesecloth. The concentrations of the resulting suspensions, which consisted mainly of microconidia, were determined with a hemacytometer and were diluted to between $1\times10^6$ and $2\times10^6$ conidia per ml and TWEEN 20 (sorbitan monolaurate polyoxyalkylene) was added at a 0.02% level, prior to application.

For Example III, inoculum of the various strains were produced in the same way as inoculum of G6 was produced for Example II.

For Examples IV and V, suspensions of conidia of *Fusarium proliferatum* strain G6 were prepared as follows: Mycelium from two-week old cultures of *Fusarium proliferatum* strain G6 were admixed with deionized water and the admixture was vortex mixed to provide a homogenized conidial suspension. The suspension was filtered through a double layer of cheesecloth and adjusted to a $1\times10^6$ conidia per ml.

In the testing of Examples I and II, the following was the case: Powdery mildew was controlled by weekly applications of sulfur. No fungicides were used to control black rot since those sufficiently compatible with the *Fusarium proliferatum* also controlled downy mildew. The *Fusarium proliferatum* suspension was applied with a SOLO backpack sprayer. The mancozeb was applied from a $CO_2$ backpack sprayer.

EXAMPLE I

In tests in 1992, two vine-plots of the downy mildew susceptible grape cultivar Chancellor were left untreated, or were sprayed at 7-day intervals with mancozeb (formulated as DITHIANE M45) at 4 lb/acre, or were sprayed to runoff at 7-day intervals with a suspension of *Fusarium proliferatum* strain G6 containing $10^6$ spores/mi. This was replicated five times. The results are set forth in Table 1 below wherein the mean percentages of clusters or cluster surface infected are followed in parentheses by the probability level at which the treatment mean is equal to the mean of the control and wherein the surface percentages do not include clusters with no infection.

TABLE 1

| Year | Treatment | % Clusters infected | % Cluster surface infected |
|---|---|---|---|
| 1992 | Control | 38.4 (1.00) | 29.3 (1.00) |
| | Mancozeb | 4.6 (0.01) | 0.3 (0.06) |
| | G6 | 26.4 (0.27) | 8.9 (0.11) |

EXAMPLE II

Testing similar to that carried out in Example I was carried out in 1993. Results are set forth in Table 2 below wherein the mean percentages of clusters or cluster surface infected are followed in parentheses by the probability level at which the treatment mean is equal to the mean of the control and wherein the surface percentages do include the clusters with no infection.

TABLE 2

| Year | Treatment | % Clusters infected | % Cluster surface infected |
|---|---|---|---|
| 1993 | Control | 43.3 (1.00) | 9.2 (1.00) |
| | Mancozeb | 0.5 (0.02) | 0.1 (0.02) |
| | G6 | 14.0 (0.07) | 1.8 (0.04) |

EXAMPLE III

Three strains of *Fusarium proliferatum* were compared in laboratory testing for efficacy against *Plasmopara viticola,* namely *Fusarium proliferatum* strains G6, C51 and C173.

The testing was carried out as follows: Ten 2-cm disks of grape leaf were each inoculated with five 10 μl droplets of a suspension of $8.5\times10^4$ sporangia of *Plasmopara viticola* per ml, and incubated at 21° C. with a 12 hour photoperiod to allow infection and sporulation. The disks were rinsed to remove existing sporangia, and then inoculated with suspension of conidia of *Fusarium proliferatum* ($1\times10^6$ conidia/ml) or distilled water (control) and then incubated for 7 days whereupon the number of sporangia of *Plasmopara viticola* produced per disk were recorded.

The results are set forth in Table 3 below and are the means of two repetitions of the experiment followed in parenthesis by the standard errors.

TABLE 3

| Strain | Sporangia × $10^3$ |
|---|---|
| G6 | 3.212 (0.554) |
| C51 | 1.950 (0.829) |
| C173 | 4.287 (1.087) |
| Control | 218.175 (43.953) |

All *Fusarium proliferatum* treatments are significantly different from the control at P=0.01.

EXAMPLE IV

Two strains of *Fusarium proliferatum* were compared in laboratory testing for efficacy in protecting against infection by *Plasmopara viticola,* namely *Fusarium proliferatum* strains G6 and M3. The testing was carried out as follows: Ten 2-cm disks of grape leaf were inoculated with a suspension of conidia of *Fusarium proliferatum* G6 or M3 ($1\times10^6$ conidia/ml), or distilled water (control), and were allowed to dry for 1 hour. The disks were then each inoculated with a 10 μl droplet of a suspension of $8.5\times10^4$ sporangia of *Plasmoapara viticola* per ml, and were incubated at 21° C. with a 12 hour photoperiod to allow for infection and sporulation for 7 days, whereupon the number of sporangia of *Plasmopara viticola* produced per disk were recorded.

The results are set forth in Table 4 below and are the means of two repetitions of the experiments followed in parentheses by the standard errors of the means.

TABLE 4

| Strain | Sporangia × $10^3$ |
|---|---|
| G6 | 24.64 (5.244) |
| M3 | 39.87 (3.810) |
| Control | 139.06 (37.816) |

The *Fusarium proliferatum* treatments are significantly different from the control at P=0.01.

EXAMPLE V

Testing of the effect of *Fusarium proliferatum* strain G6 on Arctotis sp. (Compositae), grown for flowers, infected with *Bremia lactucae* Regal, on lettuce, *Lactuca sativa* L. (Compositae), infected with *Bremia lactucae* and on *Chenopodium murale* L. (Chenopodiaceae) infected with *Peronospora farinosa* (Fr.) Fr. was carried out as follows:

Infected leaves of the plants were collected from the fields where no pesticides were applied.

For each kind of plant, five leaves (or parts of 5 leaves) with infected patches, were placed on water moisturized filter paper (Whatman No. 3) in glass deep petri dishes (9 cm diameter, 5 cm high).

Application was by spraying suspension of *Fusarium proliferatum* strain G6 to runoff using a Sigma spray assembly. After 20 hours of incubation in covered dishes at 20° C., the drops on the leaves were thoroughly dried with absorbent paper tissues. The dishes were maintained at 20° C. with a regime of 12 hour photoperiod.

The controls were leaves sprayed with deionized water.

For each kind of plant, the testing was replicated fives times.

Assessment was carried out for covering and development of *Fusarium proliferatum* strain G6 on oomycete-infected lesions, for the number of the 25 leaves parasitized with *Fusarium proliferatum* strain G6, for the coiling of hyphae of *Fusarium proliferatum* strain G6 around oomycetous pathogen conidiophores, for the spread of oomycete pathogen to healthy tissue and for the number of the 25 leaves in each control group with high amounts of development of the oomycete pathogen.

Results are set forth in Table 5 below. In Table 5, +++ stands for high amount, ++ stands for moderate amount, and + stands for low amount.

TABLE 5

| Oomycete pathogen<br>Host | *Bremia lactucae*<br>Arctotis sp. | *Bremia lactucae*<br>*Lactuca sativa* | *Peronospora farinosa*<br>*Chenopodium murale* |
|---|---|---|---|
| Covering and development of G6 oomycete-infected lesions | +++ | ++ | +++ |
| Number of 25 leaves parasitized with G6 | 23 | 20 | 24 |
| Coiling of hyphae of G6 around oomycetous pathogen conidiophores | +++ | +++ | +++ |
| Avoidance of spread of oomycetous pathogen to healthy tissue | ++ | ++ | ++ |
| Number of 25 leaves in control group with high amount of development of oomycetous pathogen | 25 | 25 | 25 |

The results show that *Fusarium proliferatum* strain G6 has activity against *Bremia lactucae* attacking two hosts and against *Peronospora farinosa* attacking *Chenopodium murale.*

*Peronospora farinosa* also attacks beet plants. Various species of Chenopodium are used as indicator plants for plant pathogenic viruses in greenhouse tests.

EXAMPLE VI

Testing was carried out as in Example V except that the testing was addressed to the effect of *Fusarium proliferatum* strain G6 on cucumber plants. *Cucumis sativus* L. (Cucurbitaceae), infected with *Pseudoperonospora cubensis* (Berk. & Curt.) Rostow and onion, i.e. *Allium cepa* L. (Liliaceae) infected with *Peronospora destructor* (Berk.) Casp.

The results are set forth in Table 6 below. In Table 6, +++ stands for high amount, ++ stands for moderate amount and + stands for low amount and 0 stands for not observed.

TABLE 6

| Oomycete pathogen<br>Host | *Pseudoperonospora cubensis*<br>*Cucumis sativus* | *Peronospora destructor*<br>*Allium cepa* |
|---|---|---|
| Covering and development of G6 oomycete-infected lesions | +++ | ++ |
| Number of 25 leaves parasitized with G6 | 21 | 19 |
| Coiling of hyphae of G6 around oomycetous pathogen conidiophores | + | 0 |
| Avoidance of spread of oomycetous pathogen to healthy tissue | + | + |
| Number of 25 leaves in control group with high amount of development of oomycetous pathogen | 16 | 22 |

The results show that *Fusarium proliferatum* strain G6 has some activity against *Pseudoperonospora cubensis* attacking *Cucumis sativus* and against *Peronospora destructor* attacking *Allium cepa*.

EXAMPLE VII

Poison agar tests were conducted in the laboratory to determine the effect of spore germination and radial growth of *Fusarium proliferatum* strain G6.

Commercial formulations of fungicides were used for testing. Various quantities of active ingredient (1, 10, 100, and 1000 ppm) were dissolved in acetone and added to potato dextrose agar at 55–60° C. For assessment of radial growth, a 6 mm diameter plug of agar containing a 10-day-old colony of *Fusarium proliferatum* strain G6 was placed in the center of each petri dish of fungicide-amended potato dextrose agar. Each treatment was replicated three times. After 10 days incubation at 20° C., colony diameter was measured. In the spore germination tests, the fungicide-amended potato dextrose agar plates were seeded with 0.2 ml of a $1\times10^5$ spores/ml suspension of microconidia. After 20 hours at 20° C., 500 spores were counted and the percent germination was calculated.

The results of the radial growth tests are set forth in Table 7 below and are the averages for the three replicates.

TABLE 7

| | Percent inhibition at each active ingredient concentration of fungicide | | | |
|---|---|---|---|---|
| Fungicide | 1 ppm | 10 ppm | 100 ppm | 1000 ppm |
| triadimefon (BAYLETON) | 58.9 | 73.1 | 79.8 | 85.2 |
| myclobutanil (NOVA) | 71.5 | 87.4 | 100.0 | 100.0 |
| benomyl (BENLATE) | 100.0 | 100.0 | 100.0 | 100.0 |
| captan (Captan) | 0.0 | 0.0 | 53.3 | 60.9 |
| dinocap (KARATHANE) | 41.1 | 40.6 | 42.6 | 48.2 |
| iprodione (ROVRAL) | 7.6 | 59.8 | 80.7 | 64.5 |
| ferbam (CARBAMATE) | 2.1 | 8.7 | 6.3 | 62.4 |
| sulfur | 11.0 | 11.7 | 11.3 | 10.2 |
| $CuSO_4$ | 0.0 | 0.0 | 0.0 | 21.9 |
| COCS | 0.0 | 0.0 | 0.0 | 74.6 |
| metalaxyl (RIDOMIL) | 4.6 | 4.6 | 4.1 | 14.3 |

TABLE 7-continued

| | Percent inhibition at each active ingredient concentration of fungicide | | | |
|---|---|---|---|---|
| Fungicide | 1 ppm | 10 ppm | 100 ppm | 1000 ppm |
| phosethyl Al (ALIETTE) | 1.1 | 2.1 | 2.6 | 62.0 |
| mancozeb (DITHANE M45) | 3.7 | 6.7 | 11.7 | 40.6 |

The results of the spore germination tests are set forth in Table 8 below.

TABLE 8

| | Percent reduction at each active ingredient concentration of fungicide | | | |
|---|---|---|---|---|
| Fungicide | 1 ppm | 10 ppm | 100 ppm | 1000 ppm |
| triadimefon (BAYLETON) | 48.6 | 52.1 | 59.5 | 64.5 |
| myclobutanil (NOVA) | 22.2 | 54.0 | 94.1 | 96.1 |
| benomyl (BENLATE) | 51.2 | 63.0 | 88.5 | 98.7 |
| captan (Captan) | 0.7 | 5.7 | 91.3 | 98.4 |
| dinocap (KARATHANE) | 42.7 | 44.7 | 80.7 | 90.9 |
| iprodione (ROVRAL) | 29.6 | 41.1 | 42.8 | 77.5 |
| ferbam (CARBAMATE) | 56.5 | 60.0 | 97.6 | 100.0 |
| sulfur | 1.5 | 8.3 | 10.0 | 10.9 |
| $CuSO_4$ | 3.8 | 5.0 | 5.5 | 11.1 |
| COCS | 15.3 | 20.2 | 23.9 | 31.9 |
| metalaxyl (RIDOMIL) | 21.4 | 35.7 | 41.5 | 42.3 |
| phosethyl Al (ALIETTE) | 43.7 | 45.4 | 50.4 | 58.4 |
| mancozeb (DITHANE M45) | 58.4 | 89.7 | 99.0 | 100.0 |

Many variations of the above will be obvious to those skilled in the art. Thus, the invention is defined by the claims.

What is claimed is:

1. A method for controlling Oomycetes species-caused plant disease comprising applying to plant surfaces to be protected an Oomycete species-inhibiting amount of *Fusarium proliferatum* wherein the Oomycetes species is from a genus selected from the group consisting of Plasmorpara, Bremia, Pseudoperonospora, Peronospora and Sclerospora.

2. The method of claim 1 wherein the plants protected are grapevines.

3. The method of claim 2 wherein the species of Oomycetes is *Plasmopara viticola.*

4. The method of claim 3 wherein the *Fusarium proliferatum* is *Fusarium proliferatum* strain G6 having accession number ATCC 74149.

5. The method of claim 3 wherein the *Fusarium proliferatum* is *Fusarium proliferatum* strain M3 having accession number ATCC 74273.

6. The method of claim 3 wherein the *Fusarium proliferatum* is *Fusarium proliferatum* strain C51 having accession number ATCC 74274.

7. The method of claim 3 wherein the *Fusarium proliferatum* is *Fusarium proliferatum* strain C173 having accession number ATCC 74275.

8. The method of claim 1 wherein the Oomycetes species is from a genus selected from the group consisting of Plasmopara, Bremia, Pseudoperonospora and Peronospora.

9. The method of claim 8 wherein the Oomycetes species is selected from the group consisting of *Plasmopara viticola, Bremia lactucae, Peronospora farinosa, Peronospora destructor* and *Pseudoperonospora cubensis.*

10. The method of claim 1 wherein the *Fusarium proliferatum* is a strain isolatable from grape leaves.

11. The method of claim 1 wherein the Oomycetes species is from a genus selected from the group consisting of Plasmopara, Bremia, Pseudoperonospora and Peronospora and the *Fusarium proliferatum* is a strain isolatable from grape leaves.

12. The method of claim 11 wherein the Oomycetes species is selected from the group consisting of *Plasmopara viticola, Bremia lactucae, Peronospora farinosa, Peronospora destructor* and *Pseudoperonospora cubensis* and the *Fusarium proliferatum* is a strain selected from the group consisting of strain G6 having accession number ATCC 74149, Strain M3 having accession number ATCC 74273, strain C51 having accession number ATCC 74274 and strain C173 having accession number ATCC 74275.

13. A method for controlling Oomycetes species-caused plant disease comprising applying to plant surfaces to be protected an Oomycetes species-inhibiting amount of *Fusarium proliferatum,* wherein the Oomycetes species is from the genus Phytophthora.

14. The method of claim 13 wherein the plants protected are potato plants.

15. The method of claim 13 wherein the species of Oomycetes is *Phytophthora infestans.*

16. The method of claim 13 wherein the *Fusarium proliferatum* is *Fusarium proliferatum* strain G6 having accession number ATCC 74149.

* * * * *